US00RE40457E

(19) United States
(12) Reissued Patent
Cavaliere ved. Vesely et al.

(10) Patent Number: US RE40,457 E
(45) Date of Reissued Patent: Aug. 12, 2008

(54) **ENTERAL DIETARY COMPOSITIONS COMPRISING A MIXTURE OF LIVE LACTIC BACTERIA CONSISTING OF *STREPTOCOCCUS THERMOPHILUS, BIFIDOBACTERIUM LONGUM* AND *BIFIDOBACTERIUM INFANTIS***

(75) Inventors: Renata Maria Anna Cavaliere ved. Vesely, Milan (IT); Claudio De Simone, Ardea (IT)

(73) Assignee: VSL Pharmaceuticals, Inc., Gaithersburg, MD (US)

(21) Appl. No.: 11/484,026

(22) PCT Filed: Jun. 3, 1997

(86) PCT No.: PCT/IT97/00127

§ 371 (c)(1),
(2), (4) Date: Jan. 27, 1998

(87) PCT Pub. No.: WO98/00035

PCT Pub. Date: Jan. 8, 1998

Related U.S. Patent Documents

Reissue of:
(64) Patent No.: 6,077,504
Issued: Jun. 20, 2000
Appl. No.: 08/952,820
Filed: Jan. 27, 1998

(30) Foreign Application Priority Data

Jun. 28, 1996 (IT) ..... MI96A1329

(51) Int. Cl.
*A01N 63/00* (2006.01)

(52) U.S. Cl. ..... 424/93.3; 424/93.44; 424/93.45
(58) Field of Classification Search ..... 424/93.3, 424/93.44, 93.45
See application file for complete search history.

(56) References Cited

U.S. PATENT DOCUMENTS 5,310,555 A * 5/1994 Zimmer ..... 424/438
5,494,664 A * 2/1996 Brassart et al. ..... 424/93.4
5,716,615 A * 2/1998 Cavaliere Vesely et al. 424/93.4

FOREIGN PATENT DOCUMENTS

EP 555618 * 8/1993
JP 01228456 * 9/1989

OTHER PUBLICATIONS

Elmer et al. "Biotherapeutic Agents". JAMA. Mar. 29, 1996, vol. 275, No. 1, pp. 870–876.*
Saavedra et al. The Lancet. Oct. 15, 1994. vol. 344, pp. 1046–1049.*
Massimo Campieri et al. Gastroenterology. May 1999, vol. 116, No. 5, pp. 1246–1249.*
A. Venteri et al. Alimet. Pharmacol. Ther. 1999. pp. 1103–1108.*
Sandborn et al. Inflammatory Bowel Disease. Feb. 1999, vol. 5, No. 1, pp. 3–39.*
Bazzocchi et al. Gastroenterology International. 1998. vol. 11, Suppl. 1.*
Gionchetti et al. Gastroenterology International. 1998. vol. 11, Suppl. 1, pp. 108–110.*

* cited by examiner

*Primary Examiner*—Vera Afremova
(74) *Attorney, Agent, or Firm*—Morgan Lewis & Bockius LLP

(57) ABSTRACT

Enteral compositions containing a mixture of live lactic bacteria consisting of *Streptococcus thermophilus, Bifidobacterium longum* and *Bifidobacterium infantis*, each at a concentration equal to or greater than $1\times10^{11}$ CFU per gram, are useful as adjuncts for enteral formulations and as oral nutritional supplements. The compositions can be administered before, during or at the end of an enteral formulation administration. The compositions can be administered separately or mixed with the enteral formulation. The compositions can also be employed at the end of the daily administration in order to prevent the colonization of the enteral tube by the other pathogens. The compositions can also be used as supplement to any liquid, creamy or pasty foodstuff.

6 Claims, No Drawings

ENTERAL DIETARY COMPOSITIONS COMPRISING A MIXTURE OF LIVE LACTIC BACTERIA CONSISTING OF *STREPTOCOCCUS THERMOPHILUS, BIFIDOBACTERIUM LONGUM* AND *BIFIDOBACTERIUM INFANTIS*

Matter enclosed in heavy brackets [ ] appears in the original patent but forms no part of this reissue specification; matter printed in italics indicates the additions made by reissue.

*This application is a reissue of U.S. application Ser. No. 08/952,820, filed on Jan. 27, 1998 and issued as U.S. Pat. No. 6,077,504, which is a U.S. national stage application under 35 U.S.C. § 371 of PCT/IT97/00127, filed Jun. 3, 1997, which claims the benefit of Italian patent application MI96A1329, filed Jun. 28, 1996.*

DESCRIPTION

The present invention relates to dietary compositions useful for enteral feeding. The present invention also relates to the use of lactic acid bacteria to prepare enteral dietary compositions adapted to modify the composition of the human intestinal flora, to stimulate the immune system or ameliorate diarrhea or intestinal disturbances. The present invention also relates to the use of a lactic acid bacteria composition as a supplementation to a foodstuff. The present invention further relates to a kit comprising two containers, one containing a foodstuff and the other containing a lactic acid bacteria composition, which shall be supplemented to said foodstuff at the moment of consuming the same.

The prior art has shown that nutritional adjunctive therapy given to patients either by mouth (enteral) or by vein (parenteral) is effective for reversing catabolism and stimulating anabolism. This improvement in the metabolic state of the patient is believed to be critical to the healing process and required for patient survival.

Numerous enteral formulations are utilized in patients with a hyper-metabolic state as effected by burns, trauma, surgery and in patients suffering from malnutrition, chronic illness and in patients suffering from disorders resulting from prolonged periods of reduced oral intake resulting from cerebral vascular accidents, gastrointenstinal diseases, or a comatose state. In general, enteral nutrition compositions may be administered orally or by tube feeding.

The use of enteral compositions (EN) has provided benefits and advantages as compared to total parenteral nutrition (TPN). The recommendation of the use of enteral compositions is based on recent clinical findings that demonstrate that the use of elemental diets results in fewer complications, reduced patient length of stay in the intensive care unit (ICU), and reduced cost, when compared to TPN.

Elemental diets are composed of low molecular weight nutrients that require minimal digestive and absorptive capability. The protein source consists of free amino acids and in particular essential and nonessential amino acids. The carbohydrate portion of such compositions is typically composed of glucose and hydrolyzed cornstarch (maltodextrin), while the fat content is usually low and primarily consists of essential fatty acids. These diets are characterized by minimal residue in the intestines, because of the efficient absorption of the nutrients provided in an elemental form.

Elemental formulations are, by nature, hyperosmolar (greater than 300 mOsm/kg $H_2O$, where mOsm= milliosmoles, the osmotic pressure of a solution is the external pressure that must be applied to a solution to prevent the diffusion of solvent from pure solvent into the solution), and can cause diarrhea. Therefore feeding is initiated using low delivery rates, which has been seen to increase the patient's tolerance.

Different enteral formulations and oral nutritional adjuncts or supplements are available i.e. ISOCAL, OSMOLITE, ENSURE, SUSTACAL, ENSURE PLUS, MAGNACAL, TRAUMACAL, ISOTEIN HN, VIVONEX T.E.N., etc.

However it has been observed that patients receiving the above mentioned nutritional regimens often have compromised defence mechanisms and abnormal intestinal flora. All that is responsible for diarrhea and other disturbances, i.e. malabsorption, flatulence, colicky pain, etc.

In recent years, attention has been focused on identifying the biochemicals and nutrients that are missing from the commercially available parenteral and enteral products. U.S. Pat. No. 5,231,085 describes a formulation designed to enhance the recovery of a deficient or suppressed immune function in humans and commercialized as IMPACT. IMPACT comprises arginine and caseinates as the protein source, maltodextrins as the carbohydrate source and menhaden oil and structured lipids as the lipids source. IMPACT therefore has been designed as a formulation specifically aimed to improve the patient's nutritional status and also their immunocompetence.

However, all previous formulations—IMPACT included—do not take into appropriate account the fact that in humans the intenstinal mucosa is unable to nourish itself from the blood and more than 80% of the energetic-nutritional demand of the large intestine must be satisfied by luminal nutrition (Roediges, W. E. W. Gut, 21:793, 1980). Sloughed intestinal epithelia, pancreatic enzymes and mucous are recycled as a nutritional source by virtue of the bacterial fermentation by the bacteria of the colon. The amount of epithelium recycled every day has been estimated to approach 300 g/day and more in some diseased states. From the above process, approximately 80 g of protein and 12–30 g of lipids each day is obtained. It is therefore apparent that, should the bacterial flora of the colon, due to antibiotic treatment or other reasons be reduced or eliminated, it would be re-supplied preferably using non-pathogenic bacteria. In ICU patients and also in patients with inflammatory bowel diseases, in AIDS patients and even in emotionally stressed individuals, the microflora is absent or heavily reduced. Even healthy-looking patients may have deficiencies in their intestinal flora or major imbalances among the different strains constituting it (Wilmore, D. W. Amer. Thorac. Soc., 55:822, 1993).

The observation that colonic mucosa cannot nourish itself from the blood is of utmost importance and explains why patients undergoing EN or TPN develop colonic mucosa atrophy within few days of the treatment (Roediges, W. E. W., Gut 21:793, 1980). As most often these patients receive antibiotics, also the flora present in the host's colon is modified or reduced. This allows potential pathogenic microorganisms to colonize the digestive system. The colonic mucosal atrophy and the overgrowth of potential pathogenic microorganisms are probably the two most important pathogenicity factors in the above mentioned patients, apart from post-operative and post-traumatic gastrointestinal disturbances, sepsis, and multiple organ failure.

IMPACT and other enteral formulations in their present form are not able and neither have they been conceived for replacing or supplementing the host's colon probiotic flora. For these reasons, diarrhea and other intestinal disturbances develop in patients treated with these products.

There is a few enteral diets containing lactobacilli. However, a low number of lactobacilli per gram or ml of composition is present. The number of lactobacilli is further reduced when these organisms pass through the gastrointestinal tract. Actually these formulations have a weak capability of promoting colonization of the colon in the treated subject.

In order to have an effect on the microflora in the intestines, attempts have been also made to select lactobacillus strains able to colonize and become established on colonic mucosa. In this context, WO 93/01823 discloses an oatmeal-based oral nutritional supplement fermented by *Lactobacillus plantarum* strain No. 299 (at a concentration of $<10^{10}$ CFU per gram of freeze-dried product) and a feeding formulation for enteral nutrition containing the same strain of *Lactobacillus plantarum* at a concentration of $1.5\times10^{6}$ CFU per 100 ml of nutrition solution, along with proteins, carbohydrates, lipids, mineral and vitamins. De facto, the disclosed composition is an enteral formulation with specific characteristics in terms of calories, proteins, fats, vitamins and minerals and supplemented with a *lactobacillus* strain. In other words, the disclosed enteral formulation is not appropriate for the needs of all individuals, as evidenced by the fact that different enteral formulations are prescribed according to different needs, as can be deduced from the following well-known classification (McClure, S., Digest. Dis. Sci., 8:1153, 1992):

A) General formulation categories:
- standard
- calorie dense
- protein dense
- elemental/semi-elemental
- short-peptide semi-elemental
- milk-based oral
- fiber enriched B) Speciality formulations:
- stress/trauma
- hepatic
- renal
- pulmonary
- diabetes
- immunostimulant.

Thus, there remains a need for enteral dietary compositions which do not suffer from the drawbacks of conventional compositions. Specifically, there remains a need for enteral dietary compositions which are effective for modifying the composition of the intestinal flora and for immunostimulation and which prevent diarrhea and intestinal disturbances. There also remains a need for enteral dietary compositions which may be used to supplement existing enteral compositions.

Moreover, taking into account the fact that in recent years there is on part of consumers an increasing demand of foodstuffs having beneficial effects in term of everyday health and prevention of diseases, the inventors have identified a new problem, namely the problem of making the use of foodstuffs containing lactic acid bacteria more easily accessible on the feed market to any consumers, either in good health or ill.

Accordingly, it is one object of the present invention to provide novel enteral dietary compositions.

It is another object of the present invention to provide novel enteral dietary compositions which are useful for immunostimulation.

It is another object of the present invention to provide novel enteral dietary compositions which are useful for modifying the composition of the intestinal flora.

It is another object of the present invention to provide novel enteral dietary compositions which exhibit a reduced tendency to cause diarrhea or intestinal disturbances.

It is another object of the present invention to provide novel enteral dietary compositions which may be used to supplement conventional enteral parenteral compositions.

It is another object of the present invention to provide a method of enteral feeding which is effective for modifying the composition of the intestinal flora.

It is another object of the present invention to provide a method of enteral feeding which is effective for immunostimulation.

It is another object of the present invention to provide a method of enteral feeding which exhibits a reduced tendency to cause diarrhea or intestinal disturbances.

It is another object of the present invention to provide a method for ameliorating diarrhea and other intenstinal or urinary disturbances caused by or associated with enteral or parenteral feeding of an elemental diet.

It is another object of the present invention to provide novel compositions comprising lactic acid bacteria, which may be used by the consumer as supplement to common foodstuffs commercially available on the feed market.

It is another object of the present invention to provide novel compositions comprising lactic acid bacteria, which may be put on the feed market in combination with the specific foodstuff, to which they shall be supplemented directly by the consumer.

These and other objects, which will become apparent during the following detailed description, have been achieved by the inventor's discovery that compositions containing two or more lactic acid bacteria selected from *Streptococcus thermophilus* and *Bifidobacterium longum*, each strain at a concentration equal to or greater than $1\times10^{11}$ CFU per gram of bacteria, do not suffer from the drawbacks of conventional enteral compositions, and may be used to modify the intestinal flora and/or stimulate the immune system of a patient in need thereof, while exhibiting a reduced tendency to cause diarrhea, intestinal or urinary disturbances.

Thus, is a first embodiment, the present invention provides enteral dietary compositions and oral nutritional supplements, which contain at least two or more lactic acid bacteria of a genus selected from the group consisting of *Streptococcus thermophilus* and *Bifidobacterium longum*. The concentration of each lactic acid bacteria is equal to or greater than $1\times10^{11}$ CFU per gram of bacteria, where CFU means colony forming unit. The concentration of each lactic acid bacteria is preferably $1\times10^{11}$ to $1\times10^{14}$ CFU/gram of bacteria, more preferably $1\times10^{11}$ to $1\times10^{12}$ CFU/gram of bacteria.

An important and novel aspect of the present invention is the fact that it is possible to modify the properties of the currently available compositions by supplementing them with a composition comprising two or more lactic acid bacteria selected from: *Streptococcus thermophilus* and *Bifidobacterium longum*, each strain at a concentration equal to or greater than $1\times10^{11}$ CFU per gram of bacteria. The composition may in addition also include one or more strains from the group consisting of *Lactobacillus acidophilus, Lactobacillus casei, Bifidobacterium bifidum, Bifidobacterium infantis, Lactobacillus plantarum*, and *Lactobacillus bulgaricus*, each at a concentration equal to or greater than $1\times10^{10}$ CFU/gram of bacteria, preferably $1\times10^{10}$ to $1\times10^{13}$ CFU/gram of bacteria.

In a preferred embodiment of the present invention, the enteral dietary composition comprises the combination of *Streptococcus thermophilus, Bifidobacterium longum* and

*Bifidobacterium infantis* at a total bacterial concentration of 0.5 to $1.5\times10^{12}$ CFU per gram of bacteria.

The bacteria can be live, freeze-dried or heat-killed (80° C. per 5 min), according to different embodiments of the invention. In the first case—live freeze-dried lactic acid bacteria—the composition may be employed to modify the ecology of the gut and to stimulate the immune system. In the second case, the heat-killed lactic acid bacteria may be used to stimulate the immune system alone or even in combination with other immunomodulants or vaccines. The problem of the survival of the live bacteria in the stomach is overcome by the high number of the bacteria, and by possible administration of the composition by naso-enteric tube, by-passing the gastric acidity. The bacteria can also be encapsulated in capsules and the patient can swallow them.

Although the present compositions are not required to contain any specific strains of the above-mentioned lactic acid bacteria, specific examples of suitable strains are set out in Table I below.

TABLE I

| Species | Accession No.[1] |
|---|---|
| *Streptococcus thermophilus* YS 52 | CNCM I-1670 |
| *Bifidobacterium longum* | ATCC 15707 |
| *Lactobacillus acidophilus* | ATCC 314 |
| *Lactobacillus casei LS1* | ATCC 25180 |
| *Bifidobacterium bifidum* | ATCC 11863 |
| *Bifidobacterium infantis* | ATCC 15697 |
| *Lactobacillus plantarum* | ATCC 8014 |
| *Lactobacillus bulgaricus* LB 1 | CNCM I-1664 |

[1]CNCM stands for Collection Nationale de Cultures de Microorganismes - Institut Pasteur, 25, Rue du Docteur Roux, 75724 Paris Cedex 15, whereas ATCC stands for American Type Culture Collection, 12301 Parklawn Drive Rockville, Maryland 20852, U.S.A.

The composition according to the present invention is preferably in a dry powder form, but it may also be prepared in any form suitable for administration to an individual in need of treatment. Thus, the composition may alternatively comprise a liquid composition comprising the lactic acid bacteria in a liquid carrier which is pharmaceutically acceptable and which is non toxic for the bacteria. The liquid carrier may comprise water, and the concentration of the bacteria will be between $1\times10^{11}$ and $1\times10^{13}$ lactic acid bacteria per ml of liquid. The liquid composition may further comprise amino acids (i.e., glutamine), sugars (i.e., dextrose), salts (i.e., sodium salts), vitamins (i.e., vitamin A), soy or corn oil, triglycerides, safflower oil and any other component suitable for enteral administrations.

The dry form of the composition preferably comprises between $1\times10^{11}$ to $1\times10^{14}$ lactic acid bacteria per gram of the total weight of the composition.

In its simplest embodiments, the composition of the present invention will comprise the bacteria in admixture with a carrier. In the preferred dry form of the invention the composition includes, in addition to the lactic acid bacteria as aforesaid, a carrier comprising the residue of a suitable growth medium for the above mentioned bacteria, which growth medium residue obviously is non-toxic to humans. The dry, powdered composition may further contain an added carrier such as aminoacids, sugars, salts, milk derivatives, inulin, oligosaccharides. In addition, the composition may contain 0 to 20 wt. %, based on the total weight of the composition, of a compatible drug, i.e., vitamins, hormones, amino acids, immune response modifiers, anti-inflammatory drugs, anti-cholinergic drugs, anti-septic drugs, adrenergic drugs and growth factors.

The present composition may be prepared by either suspending the bacteria in a liquid preparation or dry-mixing the bacteria in a powder composition.

The present compositions are advantageous as compared to those of WO 93/01823, since the present compositions contain a higher number of bacterial strains. In addition, the present compositions contain the bacteria at a concentration which is at least one order of magnitude greater than those of WO 93/01823. Moreover, the compositions of the present invention, even though they may contain different excipients, are not required to be administered as a fermented nutrient composition (i.e. in the form of oatmeal), and are expressly made to modify the properties of all enteral formulations and/or oral nutritional supplements available now and in the future.

The compositions of the present invention are also advantageous as compared to the relative feeding formulation for enteral nutrition containing the same strain of *Lactobacillus plantarum* at a concentration of $1.5\times10^{6}$ CFU in 100 ml of nutrition solution along with proteins, carbohydrate, lipids source, minerals and vitamins, since they can be added to all the commercially available formulations—general formulations and speciality formulations—changing and improving their properties. In addition, the present compositions contain more strains of bacteria and a concentration of bacteria markedly different.

Another aspect of the present invention is that the composition can be differently diluted leaving to the physician and/or the patient the liberty to select which bacteria concentration is to be fed per day, depending on the requirements of the individual and/or the disease prevention or treatment.

Last but not least, the enteral dietary compositions of the present invention may contain live freeze-dried bacteria when an immunostimulation and a modification of the composition of the intestinal flora are advisable, or heat-killed freeze-dried bacteria when only an immunostimulation is desired, along with other possible immunomodulating compounds or vaccines. The two compositions are administered by naso-enteric tube, preferentially once or twice a day, or by the oral route in a drinkable suspension or in capsules.

In another embodiment, the present invention provides a method of enteral feeding comprising feeding a patient in need thereof with the present enteral dietary composition.

Although the exact dosage of the present composition to be administered will vary with the condition and size of the patient, the exact disease or condition being treated, and the exact formulation of the composition being administered, good results have been achieved by administering the present composition in such an amount to result in the patient receiving 10 to 90%, preferably 30 to 70%, of each of *Streptococcus thermophilus* and *Bifidobacterium longum*. When using compositions which contain live bacteria, it is preferred that the composition be administered in such an amount and as such a concentration to result in the gut of the patient being populated with the bacteria contained in the composition. Thus, it is preferred that the composition be administered in such a regimen so that the patient receives $1\times10^{11}$ to $1\times10^{14}$ CFU/day, preferably $10^{11}$ to $10^{12}$ CFU/day, of the bacteria contained in the composition for a period of 1 to 365 days, preferably 1 to 90 days. For example, in the case of a composition containing $1\times10^{11}$ CFU/gram of each of *Streptococcus thermophilus* and *Bifidobacterium longum*, it is preferred that the patient receive 0.5 to 200 g, preferably 1 to 50 g, of the composition per day.

When using a composition which contains heat-killed bacteria, it is preferred that the composition be administered in such an amount and at such a concentration to result in the immunostimulation of the patient. Heat-killed bacteria too may be quantitated as CFU/g. In our hands, the best procedure was to quantitate the bacteria while alive, bring them to the desired concentration by lyophilization, and then kill them by heating. In the context of the present invention, the term "immunostimulation" means an increase of the peripheral blood lymphocyte count (≧20%) with respect to the pre-treatment value and/or an increase of ≧20% of the pre-treatment value of any parameter which is usually employed to assess specific and non-specific immunity ex vivo, i.e., TCD4 counts, immunoglobulin levels but not these parameters alone.

Typically, the administration of the composition according to the present invention will begin when the patient is unable or unwilling to consume an adequate diet, when the patient is in need of special nutritional needs (i.e., in case of renal, hepatic, cardiac diseases, cancer, etc.), when the patient has a temporary or permanent loss of the absorptive surface area of the intestine, when the patient has lost ≧10% of the usual body weight, and when the patient is immunodepressed (i.e., skin test negative, low peripheral blood lymphocyte count, low TCD4 count and other immunologic tests). The duration of the treatment will be determined by the physician and the amelioration of the clinical conditions will be observed according to the physician's clinical judgment and laboratory tests (i.e., lymphocyte counts, faecal flora examination, etc.).

Although in principle the present enteral dietary composition may be administered orally, in a preferred embodiment the present composition is fed to the patient through a naso-enteric tube. In this way, the bacteria in the present composition can more easily by-pass the acidity of the gut and survice to populate the intestines and the colon. Suitable naso-enteric tubes and the use thereof are described in Ziegler, T., *Scientific American*, November 1995, which is incorporated herein by reference.

However, due to the high concentration of the bacteria, the oral route is not excluded. In the case of compositions containing heat-killed bacteria, oral administration may be sufficient to result in immunostimulation.

As noted above, the present compositions may be as simple as a mixture of the bacteria and an acceptable excipient. In such an embodiment, it will be necessary to co-administer or co-feed an addition nutrition source, such as an enteral or parenteral dietary formulation or oral nutritional supplements. Conventional enteral and parenteral formulations are well known to those of skill i the art, and suitable examples are described in J. Parenter. Enter. Nutr., 1:14, 1993.

The conventional enteral or parenteral formulations need not necessarily be co-administered at exactly the same time as the dietary composition of the present invention. Rather, in a preferred embodiment, the conventional enteral formulation is fed through a naso-enteric tube first, followed by the feeding of the dietary composition of the present invention through the same naso-enteric tube. In this way, the bacteria of the present composition may adhere to the inside of the tube and may prevent or inhibit colonization of the tube by other, possibly pathogenic, bacteria. This same technique may be used to prevent the colonization of a catheter by pathogenic bacteria.

Moreover, the inventors have found that the composition of the present invention can be added to any liquid, creamy or pasty foodstuff, for the purpose of obtaining foods capable of increasing, supplementing and balancing the intestinal flora.

In particular the inventors have found that it is preferable for the composition of the present invention to be added to a liquid, creamy or pasty foodstuff directly by the consumer at the moment of use.

Therefore, in a further embodiment the present invention provides the use of a composition comprising two or more lactic acid bacteria selected from the group consisting of *Streptococcus thermophilus* and *Bifidobacterium longum*, each at a concentration equal to or greater than $1\times10^{11}$ CFU per gram of bacteria, as a supplementation to a liquid, creamy or pasty foodstuff, said supplementation being carried out at the moment of consuming the foodstuff.

Moreover, in a further embodiment the present invention provides a kit comprising:

a container A holding a composition comprising two or more lactic acid bacteria selected from the group consisting of *Streptococcus thermophilus* and *Bifidobacterium longum*, each at a concentration equal to or greater than $1\times10^{11}$ CFU per gram of bacteria, and a container B holding a liquid, creamy or pasty foodstuff, both said containers being closed and openable at the moment of consuming said foodstuff, and said container A being arranged for the purpose of supplementing the composition held therein to the foodstuff held in the container B at the moment of consuming said foodstuff.

Examples of foodstuffs to which the composition of the present invention can be added are products of milk and dairy industry (milk, milk-based or milk-derived products) and products based on or derived from vegetable products (in particular fruit). For example, the composition of the present invention can be added to a milk, a yoghurt, a milk-based dessert, a fruit juice, a tomato juice, a tea or any other beverage.

As already said above, in the case wherein the composition of the present invention is used as supplement to a foodstuff, it is preferable for the composition to be supplemented at the moment that the foodstuff is being consumed. In fact, if the composition were added during the production cycle of the foodstuff or when the foodstuff is being packaged, many bacteria of the composition would not keep a viable form during the preservation; moreover, during the preservation of the foodstuff, some bacteria could cause fermentations, resulting in formation of or increase in acidity, thus rendering the foodstuff inacceptable from an organoleptic point of view.

The present invention is based on the discovery that lactic acid bacteria play several important roles in the gastrointestinal tract, such as:

1) Production of nutrients for the colonic mucosa: acetate, butyrate, propionate, other short chain fatty acids, pyruvate, lactate, and amino acids such as arginine, cysteine and glutamine;
2) Production of nutrients: the B group vitamins and folic acid, antioxidants and polyamides, histamine, 5-hydrooxytryptamine, piperidine, tyramine, cadaverine, pyrrolidine, etc;
3) Elimination of toxins and unwanted substances;
4) Regulation of digestive function: mucus utilization, nutrient absorption; gastrointestinal motility, blood flow, gastrointestinal hormone secretion;
5) Host's protection against potential pathogenic microorganisms;
6) Stimulation of the immune system.

Having generally described this invention, a further understanding can be obtained by reference to certain specific examples which are provided herein for purposes of illustration only and are not intended to be limiting unless otherwise specified.

EXAMPLES

Example 1

Twenty patients ranging from 24 to 61 years of age with chronic ulcerative colitis (CUC), diarrhea and who had lost at least 10% of their body weight in the past two months were recruited into the study. The histological criteria of Lockhart-Mummery and Morson were used to establish the diagnosis of CUC and to distinguish this form of colitis from Crohn's disease. All patients at the entry in the trial were submitted to colonoscopy to assess the extend of CUC. Patents were excluded from the study if they were in treatment with antibiotics or had bacterial or parasitic pathogens in their stools, a positive test for Clostridium difficile toxin, and active viral or fungal infections as well as major clinical complications, such as megacolon, perforation, or septicaemia.

Patients complying with the study protocol received enteral composition within 72 hours of the event necessitating the admission to the hospital.

The composition was the same (ENSURE) for both groups,—Group A and Group B, except the supplementation of *Streptococcus thermophilus, Bifidobacterium longum*, and *Bifidobacterium infantis* (ratio 1:1:1) at a concentration of $1\times10^{12}$ CFU per gram of bacteria, to Group B. The bacteria were live, freeze-dried. The dosage was 6 grams of the preparation per day in only one administration. From a practical point of view, the bacteria were re-suspended in 10 ml of water and given by naso-enteric tube to the patient daily at a time included between 8 and 10 a.m., temporarily stopping the ENSURE administration. The day of entrance into the study was defined as day 0.

The required feeding interval during which the patients had to receive the formulation was 10 days, beginning with day 0. After this feeding interval, the investigator was free to provide whatever feeding was felt to be appropriate for the remainder of the hospitalization. All patients received 5-ASA (2 grams per day) as standard treatment for CUC. Patients receiving mesalamine enemas before entry in the study continued the therapy. Antibiotic treatment was not initiated during the study unless indicated, for example for pulmonary or urinary tract infections, and antibiotic-treated patients were withdrawn from the trial. Acetaminophen, H2-receptor antagonists or alumin-based antiacids were given as needed.

A complete blood count and biochemical studies, including tests of hepatic and renal function, were done at baseline and, then, at the end of the trial. Sigmoidoscopy and colonoscopy was performed at the enrollment and at the end of the trial. Faecal material was obtained at baseline and at the end of the treatment. The variable counts of bacteria were expressed as the logic10 of colony forming units (CFU/gram wet weight of faeces). Colonic mucosa specimens were randomly taken by biopsy at 5-10-15-20-25 cm from the anus during colonoscopy. Samples were both immediately frozen at −80° C. and fixed in 10% buffered formalin. For histology, 5 micron sections of paraffin-embedded tissues were stained with hematoxylin-cosin. According to the microscope features, CUC was classified in active disease (A), disease going into remission (resolving colitis) (B), and colitis in remission (C).

In specimens referred as active desease (A), mucosal capillary congestion and dilatation with intramucosal hemorrhages were prominent and associated with various degrees of epithelial necrosis and regeneration. Mucin depletion and reduction in goblet cells were present and, at the height of a severe attack, goblet cells disappeared entirely. Lymphocytes and plasma cells were present in the lamina propria, together with foci of polymorphonuclear leukocytes within the epithelial crypts, producing cryptitis, crypt abscesses, and crypt rupture.

Resolving colitis (B) exhibited reduction in the vascularity and disappearance of the acute inflammation and crypt abscesses with restoration of the goblet cell population within the epithelium and was accompanied by reactive hyperplasia of the epithelium, particularly at the base of the crypts.

Colitis in remission (C) had variable degrees of mucosal atrophy, including loss of parallelism and branching of the crypts and more severe reduction in the number of crypts per unit area and shortening of the gap between the base of the crypts and the luminal surface of the muscularis mucosae. The epithelium was frequently hyperplastic and no evidence of active inflammation was found, although some focal accumulations of lymphocytes and plasma cells could be seen.

The cytofluorographic analysis of peripheral blood mononuclear cells (PBMCs) was performed according to standard methods employing the specific monoclonal antibodies and a flow-cytometer (both reagents and flow-cytometer—Facs-scan—from Becton-Dickinson, USA).

Undesired side effects related to the administration of lactobacilli were not observed.

In the lactic acid bacteria group (Group B), at the end of the study period, four patients had colitis in remission, four resolving colitis, and two active colitis. In the control group (Group A), no amelioration was found at the end of the study period, in comparison to pretreatment. In fact, all the patients (Group A) still exhibited evidence and symptoms of active colitis.

At baseline, both groups were comparable for the presence of lactobacilli and coliforms in the faeces. However, after treatment with the ENSURE supplemented with the probiotic preparation (Group B), both lactobacilli and bifidobacteria increased significantly ($P<0.001$) whereas coliforms were significantly reduced ($P<0.01$), in comparison to Group A and to baseline values.

The results are shown in Table I.

TABLE I

Composition of colonic microflora. Mean ± standard deviation of the viable count is expressed as the log10 of CFU/wet weight of faeces.

| | COLIFORMS | LACTO-BACILLI | BIFIDO-BACTERIA |
|---|---|---|---|
| GROUP A - PRETREATMENT | 9.6 ± 4.3 | 7.2 ± 4.2 | 4.3 ± 2.1 |
| GROUP A - POST-TREATMENT | 10.7 ± 5.8 | 6.9 ± 3.9 | 3.8 ± 1.8 |
| GROUP B - PRETREATMENT | 9.5 ± 5.2 | 7.6 ± 3.6 | 4.5 ± 2 |
| GROUP B - POST-TREATMENT | 6.7 ± 2.8 | 11.9 ± 2,2(*) | 8.8 ± 1.5(*) |

(*)Statistics = p < Student's t-test for paired data

In the peripheral blood mononuclear cells (PBMCs) of patients treated with lactic acid bacteria plus ENSURE (Group B) the absolute number of activated T lymphocytes (CD3+/DR+) were increased at the end of the study period compared to pretreatment (463±173 and 203±108 cells/μl, respectively, $P<0.07$). NK cells (CD16+/CD56+) exhibited a trend towards an increase throughout all the study period, but the difference did not reach statistical significance. Cytotoxic NK-like T lymphocytes (CD3+/CD16+/CD56+) were also increased after the treatment as compared to pretreatment values (387±96 and 129±54 cells/μl, respectively, P<0.05). Taken together, these findings point out a selective expansion of the cytotoxic lymphocytes in the peripheral blood of patients, but only when treated with lactic acid bacteria plus the enteral composition (Group B). No change in PBMCs subsets was found in the group treated with the enteral composition alone (Group A).

The above-given data show that the supplemental of any enteral formulation with the composition subject of the present invention results in a modification of the intestinal flora and an amelioration of several immunological parameters.

The beneficial effects are witnessed by the improvement of the clinical conditions at the end of the trial period of patients belonging to Group B (only two with active colitis). No significant improvement was observed in Group A patients (all with active colitis).

Example 2

Twenty HIV (human immunodeficiency virus)-positive subjects who had lost at least 20% of their body weight during the preceding 4 months were recruited for study. Weight loss in HIV+ subjects was documented from information provided by the subjects and their physicians. All HIV+ subjects had Karnofsky performance scores of >50%. Exclusion criteria for HIV+ subjects included physical or functional obstruction to food intake, opportunistic infection within the preceding 30 days, and other therapies whose objectives included weight gain or increased appetite. The HIV+ subjects ranged in age from 28 to 44 years with a mean age of 35±6 years. Six individuals were either homosexual or bisexual, and the remaining 14 had histories of intravenous drug use. All subjects had maintained standard medication regimens for at least a month prior to admission and continued to do so throughout the study. All subjects were receiving antiviral therapy at the time of admission (AZT, 500 mg/day) and continued with treatment throughout the study. Sixteen patients received prophylaxis against Pneumocystic carinii prior to and during the study.

The patients were randomized in two groups and treated with NUTRINAUT, or with NUTRINAUT supplemented by the lactic acid bacteria composition for 3 weeks. The bacterial composition contained *Streptococcus thermophilus, Bifidobacterium longum*, and *Bifidobacterium infantis* (ratio 1:1:1) at a concentration of $1\times10^{12}$ CFU per gram of bacteria, heat-treated at 80° C. for 5 min. The bacteria were heat-killed and stored as a powder. The dosage was 12 grams of the composition per day in two administrations/day. From a practical point of view, the bacteria were re-suspended in 10 ml of water and given by oral route. The day of entrance into the study was defined as day 0. The required feeding interval during which the patients had to receive the composition they were randomized to was 21 days, beginning with day 0. After this feeding interval, the investigator was free to provide whatever feeding was felt to be appropriate for the remainder of the hospitalization.

The immunocompetence of the patients was assessed by measuring the number of T CD4+ cells before and after the treatment, employing a monoclonal antibody against CD4 and a flow cytometer (Becton Dickinson).

The results are reported in Table II.

TABLE II

Number of T CD4+ peripheral blood lymphocytes expressed as absolute number of cells per $mm^3$.

| | GROUP A | | GROUP B | |
|---|---|---|---|---|
| PATIENT | Before | After | Before | After |
| 1 | 122 | 132 | 213 | 262 |
| 2 | 46 | 54 | 206 | 410 |
| 3 | 267 | 343 | 101 | 158 |
| 4 | 212 | 219 | 273 | 343 |
| 5 | 254 | 223 | 240 | 398 |
| 6 | 214 | 194 | 13 | 65 |
| 7 | 275 | 186 | 146 | 163 |
| 8 | 174 | 206 | 258 | 276 |
| 9 | 251 | 279 | 179 | 182 |
| 10 | 221 | 246 | 286 | 310 |
| MEAN | 203.6 | 208.2 | 191.5 | 256.7 |
| SD | 72 | 78.3 | 85.1 | 113 |
| STATISTICS | NOT SIGNIFICANT | | | P < 0.05 |

The above data show that the patients in Group B have had an immunostimulation following the combined treatment. No significant modification was observed in patients treated with NUTRINAUT alone.

Obviously, numerous modifications and variations of the present invention are possible in light of the above teachings. It is therefore to be understood that, within the scope of the appended claims, the invention may be practiced otherwise than as specifically described herein.

We claim:

1. An enteral dietary composition, comprising:

a mixture of live lactic acid bacteria consisting of *Streptococcus thermophilus, Bifidobacterium longum* and *Bifidobacterium infantis*, wherein the *Streptococcus thermophilus* concentration is at least $1\times10^{11}$ CFU per gram, the *Bifidobacterium longum* concentration is at least $1\times10^{11}$ CFU per gram, and the *Bifidobacterium infantis* concentration is at least $1\times10^{10}$ CFU per gram, each concentration based on the total composition.

2. The composition of claim 1, wherein the *Streptococcus thermophilus* concentration is $1\times10^{11}$ to $1\times10^{14}$ CFU per gram, *Bifidobacterium longum* concentration is $1\times10^{10}$ to $1\times10^{14}$ CFU per gram, and *Bifidobacterium infantis* concentration is $1\times10^{10}$ to $1\times10^{13}$ CFU per gram, each concentration based on the total composition.

3. The composition of claim 1, which is a liquid.

4. The composition of claim 1, which is a capsule.

5. A method for stimulating the immune system or modifying the composition of human intestinal flora in vivo, comprising:

(a) preparing a composition containing a mixture of live lactic acid bacteria, said mixture consisting of *Streptococcus thermophilus, Bifidobacterium longum* and *Bifidobacterium infantis*, wherein the *Streptococcus thermophilus* concentration is at least $1\times10^{11}$ CFU per gram wherein the *Bifidobacterium longum* concentration is at least $1\times10^{11}$ CFU per gram, and the *Bifidobacterium infantis* concentration is at least $1\times10^{10}$ CFU per gram, each concentration based on the total composition; and (b) enterally administering the composition of (a) to a subject in need thereof, optionally mixed with a carrier.

6. A method for ameliorating diarrhea or intestinal disturbances in a patient in an enteral or parenteral diet feeding program, comprising:

(a) preparing a composition containing a mixture of live lactic acid bacteria consisting of *Streptococcus thermophilus, Bifidobacterium longum* and *Bifidobacterium infantis*, wherein the *Streptococcus thermophilus* concentration is at least $1\times10^{11}$ CFU per gram, the *Bifidobacterium longum* concentration is at least $1\times10^{11}$ CFU per gram, and the *Bifidobacterium infantis* concentration is at least $1\times10^{10}$ CFU per gram, each concentration based on the total composition, and (b) administering the composition of (a) to said patient, optionally mixed with a carrier.

* * * * *

UNITED STATES PATENT AND TRADEMARK OFFICE

CERTIFICATE OF CORRECTION

PATENT NO. : RE 40,457 E
APPLICATION NO. : 11/484026
DATED : August 12, 2008
INVENTOR(S) : Claudio De Simone It is certified that error appears in the above-identified patent and that said Letters Patent is hereby corrected as shown below:

Title Page, Item (75) Inventors delete "Renata Maria Anna Cavaliere ved. Vesely, Milan (IT);".

Signed and Sealed this

Twenty-fifth Day of November, 2008

JON W. DUDAS
*Director of the United States Patent and Trademark Office*